United States Patent [19]

Wagner

[11] 4,247,653
[45] Jan. 27, 1981

[54] PROCESS FOR THE PREPARATION OF LOW MOLECULAR WEIGHT POLYHYDROXYL COMPOUNDS

[75] Inventor: Kuno Wagner, Leverkusen, Fed. Rep. of Germany

[73] Assignee: Bayer Aktiengesellschaft, Leverkusen, Fed. Rep. of Germany

[21] Appl. No.: 829,167

[22] Filed: Aug. 30, 1977

[30] Foreign Application Priority Data

Mar. 30, 1977 [DE] Fed. Rep. of Germany ...... 2714104
May 11, 1977 [DE] Fed. Rep. of Germany ...... 2721093

[51] Int. Cl.³ .................. C08G 18/14; C08G 18/54; C07C 47/19
[52] U.S. Cl. .................. 521/158; 252/71; 260/410.6; 521/172; 521/173; 560/26; 560/115; 560/158; 568/678; 568/861; 568/863; 424/82; 568/388; 568/463
[58] Field of Search .......... 521/172, 158, 173, 174, 521/179, 170, 905; 568/863, 861; 260/594, 602, 590

[56] References Cited

U.S. PATENT DOCUMENTS

| | | | |
|---|---|---|---|
| 2,224,910 | 12/1940 | Hanford et al. | 528/863 |
| 2,269,935 | 1/1942 | Hanford et al. | 260/594 |
| 2,334,761 | 11/1943 | Hanford et al. | 568/863 |
| 2,351,302 | 6/1944 | Staudinger et al. | 568/863 |
| 2,760,983 | 8/1956 | MacLean et al. | 568/863 |
| 2,775,621 | 12/1956 | MacLean et al. | 568/863 |
| 2,818,443 | 12/1957 | Robeson | 260/602 |
| 3,021,289 | 2/1962 | Mueller et al. | 521/172 |
| 3,876,706 | 4/1975 | Levanersky et al. | 260/594 |

Primary Examiner—H. S. Cockeram
Attorney, Agent, or Firm—Gene Harsh; Joseph C. Gil

[57] ABSTRACT

A process is disclosed for preparing mixtures of low molecular weight polyhydroxyl compounds and hydroxyaldehydes and hydroxyketones by condensing formaldehyde hydrate with itself in the presence of (I) as catalyst a soluble or insoluble compound of a metal of the first to eighth sub-group or second to fourth main group of the Periodic System of Elements, optionally bound to a high molecular weight carrier, and (II) more than 10% by weight, based on formaldehyde, of one or more dihydric or higher hydric low molecular weight alcohols and/or higher molecular weight polyhydroxyl compounds. The pH of the reaction mixture is held at 5.5 to 9.0 until 5–40% conversion has occurred and is then lowered to between 4.5 and 8.0 (0.5–2.0 pH units lower). The reaction is then stopped by inactivating the catalyst.

15 Claims, 2 Drawing Figures

PROCESS FOR THE PREPARATION OF LOW MOLECULAR WEIGHT POLYHYDROXYL COMPOUNDS

BACKGROUND OF THE INVENTION

Polyhydroxyl compounds have become of increasing commercial importance in various fields. They are used, for example for the manufacture of non-ionic surface active compounds, as antifreezes, moisturizers and softeners, and as starting components for synthetic resins such as polyester and polyether resins on a large industrial scale.

Polyhydric alcohols are at present obtained from naturally occurring substances such as sugar or cellulose materials or synthesized by the oxidation of petroleum derivatives.

In view of the world food situation, it is undesirable to use naturally occurring substances which can serve as carbohydrate supplies for nutrition, as raw materials for industrial products. On the other hand, due to the shortage of petroleum resources, the cost of products dependent upon petroleum is constantly rising. Moreover, the supply of petroleum products is not secured over the long term. It would therefore be desirable to find manufacturing processes for polyhydroxyl compounds based on raw materials which are independent both of petroleum and of other naturally occurring nutritional substances.

Since the work of Butlerow and Loew (Ann. 120, 295 (1861) and J. pr. Chem. 33, 321 (1886)) in the previous century, it has been known that hydroxyaldehydes and hydroxyketones are formed by the condensation of formaldehyde hydrate (the term "condensation of formaldehyde" will always be used hereinafter to mean "condensation of formaldehyde hydrate with itself") under the influence of basic compounds such as calcium hydroxide or lead hydroxide. Since formaldehyde can be obtained from coal or natural gas by way of methanol, this would in theory be a way of obtaining hydroxyl compounds without the use of petroleum. These hydroxyl compounds could then be used for the synthesis of polyhydric alcohols by electrolyte reduction or catalytic or chemical hydrogeneration.

However, in spite of many proposals to synthesize polyhydroxyl compounds by the condensation of formaldehyde, no commercially satisfactory process has yet been developed for achieving this object, because it has not hitherto been possible to synthesize mixtures of polyhydroxyl compounds having a clearly specified and reproducible hydroxyl functionality and low viscosity. Moreover, the known processes give rise to mixtures of hydroxyaldehydes and hydroxyketones which are very difficult to hydrogenate and even then only with very large quantities of catalyst.

Due to the disproportionating reaction of formaldehyde to methanol and formic acid which takes place at the same time, only moderate yields have hitherto been obtainable by the known processes, so that isolation of the aqueous or aqueous/alcoholic solutions obtained was very expensive.

It is well known that the disproportionation of formaldehyde into methanol and formic acid is powerfully catalyzed by basic compounds. As stated by Pfeil, in Chemische Berichte 84, 229 (1951), the reaction velocity of this so-called Cannizzaro Reaction depends on the square of the formaldehyde concentration while the reaction velocity of formaldehyde polyaddition (C—C linkage) depends directly on the formaldehyde concentration (Pfeil and Schroth, Chemische Berichte 85, 303 (1952)). With increasing aldehyde concentration, therefore, the ratio of the desired polyhydroxyl compounds to methanol and formic acid shifts in the direction of the unwanted compounds. In most of the processes known in the art, it is therefore proposed to carry out the condensation of formaldehyde to hydroxyaldehydes and hydroxyketones in solutions which have a low formaldehyde concentration in order to keep the quantity of by-products as low as possible. However, the water used as solvent must then be removed by distillation in order to recover the hydroxyaldehydes and hydroxyketones formed in the process. This involves high energy costs due to the heat required for evaporation of the water. Processes for the condensation of formaldehyde from dilute aqueous solutions are therefore uneconomical. Moreover, if distillation is prolonged, the hydroxyaldehydes and hydroxyketones formed undergo considerable decomposition and discoloration reactions.

It would therefore be desirable to carry out the condensation of formaldehyde from the usual commercial concentrated formalin solutions or from solutions of formaldehyde in polyhydroxyl compounds which could be used later together with the other hydroxy compounds without unwanted side reactions appearing during the condensation reaction.

A process for the preparation of aliphatic hydroxyaldehydes in which a 40% formalin solution is reacted with thallium or thallium hydroxide has been described in German Pat. No. 822,385, but this process is dangerous because of the toxicity of thallium, and the fact that thallium hydroxide is difficult to obtain. Moreover, the yields of this process are relatively low, being only 70 to 80%.

It has also been proposed to prevent the Cannizzaro reaction by reacting formaldehyde solutions with calcium or lead hydroxide in the presence of methanol, ethanol or other polar organic solvents as described in German Pat. No. 830,951 and Gorr and Wagner, Biochemische Zeitschrift, 262, 361 (1933).

This addition or organic solvents, however, reduces the formaldehyde content of the solution. The additional energy costs required for evaporating the additional solvent to isolate the hydroxyaldehydes and ketones would therefore indicate that this process is also uneconomic. Moreover, formaldehyde and lower alcohols react to form unstable semiacetals which decompose during the condensation process with spontaneous liberation of the alcohols. The consequent delays in boiling which occur if the condensation reactions are carried out at reaction temperatures above the boiling point of the alcohol give rise to violent phenomena, particularly in large reaction batches. The condensation process is somewhat dangerous when carried out on a commercial scale under these conditions.

A process for the preparation of oxy-oxo compounds in which aqueous formaldehyde solutions at concentrations of up to 30% are reacted with lead oxide or lead acetate and inorganic bases to form sugar-like compounds which reduce Fehling's solution in the cold has been described in German Pat. No. 884,794. In this process, however, the formaldehyde solution must be heated for from 7 to 8 hours. The volume/time yield is therefore not satisfactory. The relatively low yields of approximately 80%, based on the quantity of formaldehyde put into the process, are also by no means satisfactory.

A process for the preparation of hydroxyaldehydes and hydroxyketones has been disclosed in U.S. Pat. No. 2,224,910 in which the exothermic condensation of formaldehyde is regulated by the controlled addition of inorganic or organic bases to a formaldehyde solution containing lead, tin, calcium, barium, magnesium, cerium or thorium compounds as well as a compound which is capable of enediol formation, such as glucose, ascorbic acid, fructose, benzoin, glycol aldehyde, erythrose, reductose, invert sugar or condensation products of formaldehyde. Although this process makes it possible for a mixture of hydroxyaldehydes and hydroxyketones to be obtained from relatively highly concentrated formaldehyde solutions without the addition of organic solvents, it involves various disadvantages. If the reaction is carried out at a low pH, the reaction product consists mainly of hydroxyaldehyde and hydroxyketone mixtures which have a low hydroxyl functionality. Moreover, only moderate reaction velocities are obtained at low pH values, so that the volume/time yields of this variation of the process are not satisfactory. To overcome these disadvantages, it is recommended in the cited Patent Specification to start the formaldehyde condensation reaction at low pH values and then complete it at higher pH values. However, at pH values at or above 7, lead catalyzed formaldehyde condensation proceeds so rapidly, spontaneously and uncontrollably that it is impossible to obtain mixtures of hydroxyaldehydes and hydroxyketones with a reproducible distribution of components by this process because the reaction times and conditions can no longer be accurately controlled. Furthermore, it is known that hydroxyaldehydes, hydroxyketones and monosaccharides decompose in an alkaline medium at elevated temperatures to dark colored compounds partly containing carboxyl groups.

These decomposition reactions occur particularly in those methods described in U.S. Pat. No. 2,224,910 which are suggested as preferred variations, and they occur to the greatest extent when most of the formaldehyde has already reacted. Hydroxyaldehyde and hydroxyketone mixtures prepared according to the process of U.S. Pat. No. 2,224,910 therefore contain decomposition products with acid groups, are brown in color and cannot be obtained reproducibly. Moreover, hydrogeneration of these mixtures requires unecomically large quantities of Raney nickel catalyst. 30 g of Raney nickel are required to hydrogenate a quantity of hydroxyaldehyde and hydroxyketone mixture equivalent to 100 g of formaldehyde.

In addition, the product mixtures obtained by the procedure described above must always be processed by distillation to purify them and recover hydroxyl compounds with a low molecular weight. It would, however, be desirable to dispense with the distillative working up of the mixture. Since this involves additional consumption of energy and cost of apparatus. It would be preferable to prepare the product mixtures in such a way that they could be used without further distillation as soon as the water of solution has been removed. However, such colorless reaction mixtures substantially free from by-products cannot be obtained by the process known in the art.

It is therefore an object of the present invention to provide a process for synthesizing mixtures of polyhydroxyl compounds which are as far as possible free from decomposition products and which can easily by hydrogenated to polyhydric alcohols with small quantities of hydrogenation catalysts or used directly for the production of polyurethane resins. The mixtures of polyhydroxyl compounds obtained should be colorless and require no further purification and have as low a viscosity as possible.

It is also an object of this invention to control the condensation of formaldehyde so that the distribution of products in the resulting mixtures of low molecular weight polyhydroxyl compounds can be varied as desired and obtained reproducibly.

DESCRIPTION OF THE INVENTION

It was suprising and completely unexpected to find that mixtures of hydroxyaldehydes and hydroxyketones and of polyhydric alcohols which are free from reducing groups, in which mixtures the proportion of polyhydric alcohols (produced by a crossed Cannizzaro reaction) is preferably from 30 to 75% by weight, can be prepared with excellent volume/time yields if the condensation of formaldehyde hydrate is carried out in the presence of the following substances, preferably without the use of organic solvents:

(1) Soluble or insoluble compounds of metals of the 1st to 8th sub-Group or 2nd to 4th Main Group of the Periodic System of Elements, preferably lead, tin, calcium, barium, magnesium, cerium or thorium compounds used as catalysts, which may be bound to high molecular weight carriers, (2) one or more monohydric or, preferably polyhydric low molecular weight alcohols and/or higher molecular weight polyhydroxyl compounds and optionally, (3) compounds capable of enediol formation as cocatalysts. It is advantageous that the polyhydroxyl compounds used as reaction medium need not subsequently be removed. Furthermore, the products obtained are not colored and no retardation of boiling occurs.

The reaction temperature during formaldehyde condensation is generally between 10° and 150° C., preferably, between 70° C. and 120° C., more preferably between 90° C. and 110° C. The pH is controlled by controlled addition of bases so that it is between 5.5 and 9.0, preferably between 6.5 and 8.5, up to a conversion of the starting materials of from 5 to 40%, preferably from 10 to 20%, and thereafter between 4.0 and 8.0, preferably between 5.5 and 7.5 until termination of the condensation reaction. The pH during this phase of the reaction preferably is lower by 0.5 to 3, more preferably by 1 to 2 units than in the first phase of the reaction.

The present invention thus relates to a process for the preparation of mixtures of low molecular weight polyhydroxyl compounds and optionally hydroxyaldehydes and hydroxyketones by the condensation of formaldehyde in the presence of from 0.01 to 10% by weight, based on the quantity of formaldehyde, of metal compounds as catalysts and from 0 to 10% by weight, based on the quantity of formaldehyde, of cocatalysts based on compounds capable of enediol formation, which process is characterized in that aqueous formalin solutions and/or paraformaldehyde dispersions containing from 20 to 65% by weight of formaldehyde are condensed at a reaction temperature of from 10° to 150° C., preferably 70° to 120° C., more preferably 90° to 110° C., in the presence of (I) a soluble or insoluble compound of a metal of the 1st to 8th sub-Group or of the 2nd to 4th Main Group of the Periodic System of Elements, which may be bound to a high molecular weight carrier, and

(II) more than 10% by weight, based on the quantity of formaldehyde, of one or more monohydric or polyhydric low molecular weight alcohol(s) and/or higher molecular weight polyhydroxyl compounds, in which process the pH of the reaction solution is maintained at between 5.5 and 9.0, preferably between 6.5 and 8.5 by controlled addition of one or more inorganic and/or organic bases up to a conversion rate of the starting materials of from 5 to 40%, preferably 10 to 20%, and thereafter at between 4.0 and 8.5, preferably between 5.5 and 7.5 until termination of the condensation reaction so that in this second phase of the reaction is pH preferably is lower by 0.5 to 3.0 units than in the first phase of the reaction, and the reaction is stopped when the residual formaldehyde content is from 0 to 10% by weight, preferably from 0.1 to 6% by weight, by inactivation of the catalyst in known manner, e.g. by the addition of acid, and the catalyst is then removed, preferably either by precipitation reactions or by cathodic electrochemical deposition, and the aldehyde and keto groups in the reaction product are then optionally reduced to hydroxyl groups.

It is known to reduce hydroxyaldehydes and hydroxyketones with formaldehyde. Thus, for example, pentaerythritol can be synthesized from acetaldehyde and formaldehyde, the acetaldehyde first being methylolated to pentaerythrose and then reduced with excess formaldehyde. Such crossed Cannizzaro reactions can only be carried out in a strongly alkaline medium. It was therefore extremely surprising to find that in the new process, this reduction proceeds to yields of 30 to 75% in both a weakly alkaline medium and in a slightly acid medium. This reduction advantageously already reduces a high proportion of carbonyl groups, thereby considerably simplifying the subsequent removal of the remaining carbonyl groups by hydrogenation or reduction.

It was also surprising to find that the reaction carried out according to the invention results in highly concentrated aqueous solutions of hydroxyaldehydes and hydroxyketones which are pale or colorless and require no purification. In the processes known in the art, on the other hand, undesirable, strongly colored by-products are formed due to decomposition reactions. The removal of these by-products is very difficult if not impossible. Moreover, these strongly colored solutions obtained by the known processes of the art are impossible or, at least, very difficult to hydrogenate to polyhydric alcohols. At best only low yields can be obtained. On the other hand, the reaction mixtures obtained according to the invention are able to undergo catalytic hydrogenation under the mild conditions normally employed for the catalytic hydrogenation of sugars, after the catalyst which contains lead has been removed by a simple precipitation reaction or by electrochemical deposition.

In the process according to the invention, glycol aldehyde is first formed from two molecules of formaldehyde in a primary reaction step. Glyceraldehyde is then formed from the glycol aldehyde by further addition of formaldehyde hydrate as represented by the following reaction scheme:

The mixtures of the hydroxyaldehydes and ketones obtained according to the invention are then formed glyceraldehyde by numerous subsequent reactions, some of which are shown as examples below:

-continued

Gas chromatograhic analysis of various product mixtures prepared according to the invention has shown that the distribution of products obtained by the process according to the invention can be varied by stopping the reaction at various residual formaldehyde contents and that the distribution of products can be adjusted to be completely reproducible both with respect to compounds having from 2 to 4 carbon atoms and with respect to compounds having 5 or more carbon atoms. This was not to be expected in view of the large number of reactions, only some of which have been mentioned above, which may take place simultaneously and side by side in the process according to the invention.

The condensation of formaldehyde by the process according to the invention is preferably carried out with aqueous formaldehyde solutions at commercial concentrations (30 to 50% by weight formaldehyde) stabilized with methanol or other known stabilizers. However, unstabilized formaldehyde solutions containing a proportion of solid, polymerized formaldehyde and/or para-formaldehyde dispersions may also be used since these solid constituents are dissolved by depolymerization during the process according to the invention and can then also be condensed to hydroxyaldehydes and hydroxyketones. Even more highly concentrated formaldehyde solutions such as these obtained by depolymerization of paraformaldehyde or by concentration of dilute formaldehyde solutions by evaporation under vacuum can also be condensed by the process according to the invention. For example, hydroxyaldehydes and hydroxyketones can be obtained in very high yields by condensation of a 65% formaldehyde solution which has been obtained by evaporating a 37% formaldehyde solution under vacuum. The process according to the invention may, of course, also be applied to less highly concentrated formaldehyde solutions, but these more dilute formaldehyde solutions are less desirable from an economic point of view, on account of the additional energy costs required for evaporation of the solvent.

Hydroxyaldehydes and hydroxyketones are formed extremely rapidly in the process according to the invention. After a reaction time of 15 minutes, for example, about 80% of the formaldehyde put into the process has generally undergone reaction, and after 20 minutes the formaldehyde content of the solution is generally reduced to 1 to 1.5%, which corresponds to a conversion of 96 to 97%. The volume/time yields of the process according to the invention are therefore superior to those of all known processes for the preparation of hydroxyaldehydes and hydroxyketones by condensation of formaldehyde. Compared with the processes mentioned in German Pat. No. 884,794, for example, the volume/time yield is greater by a factor of 25 to 50.

According to the invention, the condensation of formaldehyde to hydroxyaldehydes and hydroxyketones is preferably catalyzed by water-soluble compounds of lead, in particular lead(II) acetate, lead(II) formate and lead(II) nitrate. Since commercial formaldehyde solutions are normally slightly acid in reaction, lead compounds which are insoluble in water, such as lead(II) carbonate, lead(II) oxide, and lead(II) hydroxide and lead(II) salts of oxalic acid, phenol, thiophenol or salicylic acid may also be used as the catalyst.

The following are examples of other compounds which may be used as catalysts: $AgNO_3$, $Cu(NO_3)_2$, $Ca(OH)_2$, $Mg(OH)_2$, $Mg(NO_3)_2$, $Ba(NO_3)_2$, $SnCl_2$, $Sn(OH)_2$, $Hg(NO_3)_2$, $CeCl_3$ and $Th(NO_3)_3$.

According to the invention, the quantity of catalyst used is approximately 0.01 to 10% by weight, preferably 0.1 to 5% by weight, based on the quantity of formaldehyde put into the process. Compounds of divalent lead or also of tetravalent lead are particularly preferred, as already mentioned above.

In the process according to the invention, the lead(II) ions are generally removed by precipitation with carbonate ions before the reaction products are worked up or hydrogenated. It is particularly advantageous, and very desirable for environmental reasons, that these precipitated lead salts can be used again as catalysts, either as such or after conversion to the acetate. The ecologically potentially harmful waste products resulting from the processes known in the art are thus avoided in the process according to the invention. The process is therefore superior to the known processes both on ecological and on economic grounds in view of the recycling of the lead catalyst.

The lead(II) ions used as catalyst can also be removed as elementary lead by electrolytic cathodic deposition. In that case, the lead can be returned to the production process as catalyst, for example by conversion into the acetate or by anodic oxidation accompanied by solution.

The lead(II) ions can also be removed from the reaction solution quite simply by pumping the solution over cation active ion exchanger. Analysis by atomic absorption shows that no lead can be detected in a reaction solution which has been treated in this way.

Ion exchangers which have become partly or completely charged with lead in the process of purification or removal of lead from the reaction solution and ion exchangers which have been deliberately charged with lead ions by a directed stream of lead salt solution can also be used as catalysts for the condensation of formaldehyde under the conditions of the process according to the invention. It has been found that these lead charged ion exchanger resins, (e.g. the known sulphonated polystyrene resins cross-linked with divinylbenzene, or cross-linked acrylic acid resins or modified formaldehyde urea derivatives) are just as successful in catalyzing formaldehyde condensation as the soluble lead salts themselves. It is particularly advantageous that the quantities of lead used in these ion exchangers can be much smaller than the quantities required in the known processes. It is also advantageous that these lead charged ion exchangers can be obtained directly from the removal of salt from the reaction solution and used again for the removal of salt after they have been used as catalysts.

According to a particularly advantageous embodiment of the process according to the invention, the following procedure is adopted: A certain quantity of lead charged ion exchanger resin, depending on the quantity of reaction mixture used, is added as solid catalyst to the reaction solution. Lead ions are given off to the reaction solution during the reaction so that the solid catalyst gradually becomes depleted of lead ions. After termination of the reaction, the ion exchanger is removed by suction filtration and the reaction solution is freed from lead by passage over an ion exchanger which is not charged or only partly charged with lead. After repeated use, that part of the ion exchanger resin which was used as solid catalyst is so severely depleted of lead ions that its catalytic activity is slightly reduced.

The other part of the ion exchanger resin, which was used for removing the lead from the solution, is now heavily charged with lead ions. When both parts of the exchanger resin have been rinsed with water, that part which was used for removal of the lead from the reaction solution is now used as catalyst while the other part, which is no longer completely charged with lead, is used for removing lead ions from the reaction mixture.

In this way, the lead required for catalysis can be completely utilized without fresh lead salts having to be repeatedly added or any harmful waste products being formed. This variation of the process is therefore particularly interesting both for economic and for ecological reasons.

What has been said above about lead compounds is, of course, similarly applicable to compounds of other metals used as catalysts.

According to another, particularly simple method by which the catalyst metal, in particular lead, can be used repeatedly for the condensation process, the metal ions are deposited electrolytically on a metal cathode after formaldehyde condensation has been stopped by the addition of acid, the reaction chamber is then emptied, fresh formalin solution is introduced, optionally with the addition of cocatalyst, the polarity of the current is reversed so that the electrode previously functioning as cathode becomes the anode, and the metal deposited in metallic form on the electrode which is now the anode is reconverted into metal ions by anodic oxidation and these metal ions go into solution. This process can be repeated indefinitely since no metal is lost.

A special feature of the process according to the invention is the use of relatively large quantities of monohydric or polyhydric low molecular weight alcohols and/or higher molecular weight polyhydroxyl compounds. This procedure affords important advantages. Firstly, it considerably facilitates the complete removal of water from the product mixture by evaporation under vacuum. Furthermore, reaction temperatures above 100° C. may be employed, so that the volume/time yield is improved.

The viscosity of the product is also surprisingly found to be considerably lower than that of formaldehyde condensation products produced without the addition of the above mentioned compounds according to the invention. The processing characteristics of the products are thereby substantially improved. The products obtained according to the invention are compatible with many other starting components used for the production of polyurethane resins, particularly foam resins, e.g. polyethers, polyesters and blowing agents. This is particularly surprising in view of the fact that, when previously known polyols prepared by formaldehyde condensation reactions are mixed with blowing agents, flocculation and cloudiness are observed. The miscibility of the individual components can be even further improved in the process according to the invention by adding known emulsifiers, anticoagulants and stabilizers for emulsions, dispersions and suspensions.

The quantity of monohydric or polyhydric alcohol or higher molecular weight polyhydroxyl compound used as reaction medium according to the invention may vary within wide limits, depending on the purpose for which the end product is to be used. It is advantageous to use more than about 10% by weight thereof, or 0.1 hydroxyl equivalents, based on the quantity of formaldehyde. There is no upper limit which must be observed. The limit is chosen in any individual case depending on the quantity of additional polyhydroxyl compound desired for the particular polyurethane formulation. Quantities of between 20% by weight and 500 hydroxyl equivalents, based in each case on the quantity of formaldehyde are preferably used. If more than 500 hydroxyl equivalents of polyhydroxyl compounds are used, based on 1 mol of formaldehyde, it is generally no longer possible to follow the conversion of formaldehyde accurately.

Low molecular weight alcohols within the meaning of the present invention are alcohols having a molecular weight of between 62 and 400 and having from 1 to 8, preferably 2 to 6, hydroxyl groups. The alcohols are preferably liquid at room temperature either on their own or when mixed with formalin solution. Alcohols which have at least two adjacent hydroxyl groups are particularly preferred.

The following are examples of low molecular weight alcohols in which condensation of formaldehyde can readily be carried out: 2-Ethoxyethanol; 2-propoxyethanol; 2-isopropoxyethanol; 2-butoxyethanol; 2-(2-methoxyethoxy)-ethanol; 2-(2-ethoxyethoxy)-ethanol; 1,2-bis-(2-hydroxyethoxy)-ethane; ethane glycol; diethylene glycol; triethylene glycol; tetraethyleneglycol; 1,2-propanediol; dipropyleneglycol; tripropylene glycol; 1,3-propanediol; 1,2-butanediol; 1,3-butanediol; 2-methoxy-1-butanol; 2,3-butanediol; 1,5-pentanediol; 2,2-dimethyl-1,3-propanediol; 1,6-hexanediol; 2,5-hexanediol; 2-methyl-2,4-pentanediol; 3-methyl-1,5-pentanediol; 3-methyl-2,4-pentanediol; 2,3-dimethyl-2,3-butanediol; 2-methyl-2-propyl-1,3-propanediol; 2,2-diethyl-1,3-propanediol; 2-ethyl-1,3-hexanediol; 2,5-dimethyl-2,5-hexanediol; 2,2,4-trimethyl-1,3-pentanediol; 1,3-diethoxy-2-propanol; 2-hydroxymethyl-2-methyl-1,3-propanediol; 1,2,6-hexanetriol; 2-ethyl-2-hydroxymethyl-1,3-propanediol; 2,2-bis-hydroxymethyl-1,3-propanediol; erythritol; quinitol; mannitol; sorbitol and methyl glycoside, and ethoxylation and propoxylation products of these alcohols with molecular weights of up to 400 and, of course, also mixtures of these alcohols. Ethylene glycol, glycerol and 1,4-butanediol as well as sugar alcohol mixtures obtained by a crossed Cannizzaro reaction during formaldehyde condensation are particularly preferred.

Higher molecular weight polyhydroxyl compounds within the meaning of the present invention are those with molecular weights from 400 to 10,000, preferably 500 to 600. They may be used according to the invention for formaldehyde condensation, optionally as mixtures with the above-mentioned alcohols. These polyhydroxyl compounds are also preferably liquid at room temperature or soluble in the aqueous formaldehyde solution. They include, for example, polyesters, polyethers, polythioethers, polyacetals, polycarbonates and polyester amides having at least 2, generally 2 to 8, preferably 2 to 4 hydroxyl groups, such as the hydroxyl compounds known per se for the production of both homogeneous and cellular polyurethanes.

Suitable polyesters with hydroxyl groups include, for example, reaction products of polyvalent, preferably divalent alcohols, to which trivalent alcohols may be added, and polyvalent, preferably divalent carboxylic acids. Instead of free polycarboxylic acids, the corresponding polycarboxylic acid anhydrides or corresponding polycarboxylic acid esters of lower alcohols or mixtures thereof may, of course, be used for preparing the polyesters. The polycarboxylic acids may be aliphatic, cycloaliphatic, aromatic and/or heterocyclic and they may be substituted, e.g. by halogen atoms, and/or unsaturated.

The following are mentioned as examples: Succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid which may be mixed with monomeric fatty acids, dimethyl terephthalate and terephthalic acid-bis-glycol esters. The following are examples of suitable polyvalent alcohols: Ethylene glycol, propylene glycol-(1,2) and -(1,3), butylene glycol-(1,4) and -(2,3), hexanediol-(1,6), octanediol-(1,8), neopentylglycol, cyclohexanedimethanol (1,4-bis-hydroxymethylcyclohexane), 2-methyl-1,3-propanediol, glycerol, trimethylolpropane, hexanetriol-(1,2,6), butanetriol-(1,2,4), trimethylolethane, pentaerythritol, quinitol, mannitol and sorbitol, methylglycoside, diethylene glycol, triethylene glycol, tetraethylene glycol, polyethylene glycols, dipropylene glycol, polypropylene glycols, dibutylene glycol and polybutylene glycols. The polyesters may also contain a proportion of carboxyl end groups. Polyesters of lactones such as ε-caprolactone or hydroxycarboxylic acids such as ω-hydroxycaproic acid may also be used.

The polyethers used according to the invention which have at least 2, generally 2 to 8 and preferably 2 to 3 hydroxyl groups are also known per se. They are prepared, for example, by polymerization of epoxides such as ethylene oxide, propylene oxide, butylene oxide, tetrahydrofuran, styrene oxide or epichlorohydrin, either each on its own, e.g. in the presence of boron trifluoride, or by addition of these epoxides, either as mixtures or successively, to starting components having reactive hydrogen atoms. These starting components include water, alcohols, ammonia or amines, e.g. ethylene glycol, propylene glycol-(1,3) or (1,2), trimethylolpropane, 4,4'-dihydroxy-diphenylpropane, aniline, ammonia, ethanolamine or ethylene diamine. Sucrose polyethers may also be used according to the invention, e.g. those described in German Auslegeschriften 1,176,358 and 1,064,938. It is in many cases preferred to use polyethers which contain predominantly primary hydroxyl groups; up to 90% by weight, based on all the hydroxyl groups present in the polyether. Polyethers modified with vinyl polymers, e.g. the compounds obtained by polymerization of styrene or acrylonitrile in the presence of polyethers (U.S. Pat. Nos. 3,383,351; 3,304,273; 3,523,093 and 3,110,695 and German Pat. No. 1,152,536) are also suitable, as well as polybutadienes which have hydroxyl groups.

Particularly suitable among the polythioethers are the condensation products obtained by reacting thiodiglycol on its own and/or with other glycols, dicarboxylic acids, formaldehyde, aminocarboxylic acids or amino alcohols. The products obtained are polythio mixed ethers, polythio ether esters or polythio ether ester amides, depending on the cocomponents.

Suitable polyacetals include, for example, the compounds which can be prepared from glycols such as diethylene glycol, triethylene glycol, 4,4'-dioxethoxydiphenyl dimethylmethane, hexanediol and formaldehyde. Suitable polyacetals for the purpose of the invention may also be prepared by the polymerization of cyclic acetals.

The polycarbonates with hydroxyl groups used may be of the kind known per se, for example those which can be prepared by the reaction of diols such as propanediol-(1,3), butanediol-(1,4) and/or hexanediol-(1,6), diethylene glycol, triethylene glycol or tetraethylene glycol with diarylcarbonates, e.g. with diphenylcarbonate or phosgene.

Suitable polyester amides and polyamides include, for example, the predominantly linear condensates prepared from polyvalent saturated and unsaturated carboxylic acids or their anhydrides and polyvalent saturated and unsaturated amino alcohols, diamines, polyamines and mixtures thereof.

Polyhydroxyl compounds already containing urethane or urea groups and modified or unmodified natural polyols such as castor oil, carbohydrates or starch may also be used. Addition products of alkylene oxides and phenol formaldehyde resins or of alkylene oxides and urea formaldehyde resins are also suitable for the purpose of the invention.

Representatives of these compounds which may be used according to the invention have been described, for example, in High Polymers, Vol. XVI, "Polyurethanes, Chemistry and Technology" by Saunders-Frisch, Interscience Publishers, New York, London, Volume I, 1962, pages 32–42 and pages 44–54 and Volume II, 1964, pages 5–6 and 198–199 and Kunststoff-Handbuch, Volume VII, Vieweg-Höchtlen, Carl-Hanser-Verlag, Munich, 1966, e.g. on pages 45 to 71.

Mixtures of the above mentioned compounds which contain at least two hydrogen atoms capable of reacting with isocyanates and have a molecular weight of from 400 to 10,000 may, of course, also be used, for example mixtures of polyethers and polyesters.

Polyhydroxyl compounds which contain high molecular weight polyadducts or polycondensates in a finely dispersed or dissolved form may also be used according to the invention. Such modified polyhydroxyl compounds are obtained when polyaddition reactions (e.g. reactions between polyisocyanates and aminofunctional compounds) or polycondensation reactions (e.g. between formaldehyde and phenols and/or amines) are carried out in situ in the above mentioned hydroxyl compounds. Processes of this kind have been described, for example, in German Auslegeschriften 1,168,075 and 1,260,142 and German Offenlegungsschriften 2,324,134; 2,423,984; 2,512,385; 2,513,815; 2,550,796; 2,550,797; 2,550,833 and 2,550,862. According to U.S. Pat. No. 3,896,413 or German Offenlegungsschrift 2,550,860, modified polyhydroxyl compounds of this kind can also be obtained by mixing a previously prepared aqueous polymer dispersion with a polyhydroxyl compound and then removing the water from the mixture.

When such modified polyhydroxyl compounds are used as starting components for the polyisocyanate polyaddition process, polyurethane resins with substantially improved mechanical properties are in many cases obtained.

It is not necessary according to the invention but often preferred for the sake of accelerating the reaction to include, among the components used for the condensation reaction of formaldehyde, compounds which are capable of enediol formation and which therefore acts as cocatalysts. Suitable cocatalysts for this purpose include, for example, those mentioned in U.S. Pat. No. 2,224,910, such as glycol aldehyde, glyceraldehyde, erythrose or glucose. The preferred cocatalysts according to the invention, however, are mixtures of hydroxyaldehydes and hydroxyketones such as are formed in the condensation of formaldehyde. These mixtures contain at least 75% by weight of compounds containing from three to six carbon atoms and are characterized by the following molar ratios: Compounds with 3 carbon atoms/compounds with 4 carbon atoms:

0.5:1–2.0:1

Compounds with 4 carbon atoms/compounds with 5 carbon atoms:

0.2:1–2.0:1

Compounds with 5 carbon atoms/compounds with 6 carbon atoms:

0.5:1–5.0:1

Cocatalysts of this type and their preparations have been described in German Offenlegungsschrift No. 2,639,084. According to the invention, these cocatalysts are used in quantities of from 0.1 to 10% by weight, most preferably 0.5 to 5% by weight, based on the quantity of formaldehyde used.

It has surprisingly been found that the condensation reaction according to the invention will take place sufficiently rapidly even without one of the cocatalysts described above if the reaction mixture contains more than 10% by weight, preferably more than 20% by weight of polyhydric alcohols having at least two adjacent hydroxyl groups. If, therefore, the process according to the invention is to be carried out without the addition of cocatalysts, it is preferable to use a reaction mixture containing such larger quantities of polyhydric alcohols having at least two adjacent hydroxyl groups.

Since the condensation of formaldehyde to hydroxyaldehydes and hydroxyketones takes place so rapidly at temperatures above 95° C. under the conditions according to the invention that the reaction mixture is heated by the heat of reaction liberated, the reaction solution need only be heated externally to temperatures of from 90° to 100° C., and the external source of heat may then be removed. The quantities of heat liberated by the exothermic reaction are so great that the reaction solution is easily kept at boiling point during the whole of the reaction. At the same time, the reaction velocity is still sufficiently low within the given pH range to make it possible for the reaction to be stopped at any time by external cooling or by the addition of acids if this is desirable for obtaining a particular residual formaldehyde content or distribution of products.

The pH control as carried out according to the invention is also particularly advantageous because, within this range, the reaction velocity can very easily be controlled by slight changes in pH. If excessive quantities of heat causing vigorous boiling are nevertheless produced, they can easily be removed by external cooling.

Inorganic bases suitable for the process according to the invention include, for example, NaOH, KOH, CaO, Ca(OH)$_2$, MgO and Mg(OH)$_2$. Urotropine, pyridine, secondary and tertiary amines and so-called crown ether complexes of alkali metals are examples of suitable organic bases.

Higher molecular weight polyols, hydroxyaldehydes and hydroxyketones, particularly with five and six carbon atoms, are obtained without undesirable colored by-products in the process according to the invention if the reaction is continued to a residual formaldehyde content of from 0 to 1.5% by weight and then stopped by cooling and/or by inactivation of the catalyst. The product mixtures obtained in this way are substantially free from formaldehyde.

As shown by gas chromatographic analysis of the hydrogenated and silylated reaction products, in the above mentioned preferred variation of the process according to the invention, in which the reaction is continued to a residual formaldehyde content of from 0 to 1.5% by weight, the proportions of alcohols formed, (if the proportion of alcohol or alcohol mixture previously added is subtracted from the overall composition of the product) include approximately 45% by weight of hexavalent alcohols, 27% by weight of pentavalent alcohols and approximately 7% by weight of heptavalent and higher valent alcohols. The proportion of dihydric, trihydric and tetrahydric alcohols together amounts to only about 22% (see Example 1). In the processes known in the art, for example that described in U.S. Pat. No. 2,224,910, the proportion of these low molecular weight constituents amounts to over 60%.

The process according to the invention is not restricted to the preparation of mixtures of hydroxyaldehydes and hydroxyketones and polyhydric alcohols with a predominant proportion of higher functional compounds. As already mentioned above, the distribution of products can be varied according to the invention by continuing the condensation reaction to a certain residual formaldehyde content and then stopping it, for example by cooling and/or inactivation of the catalyst. If, for example, the condensation reaction is only continued to the stage where the solution still contains 8% by weight of free formaldehyde and the reaction mixture is then cooled, practically no compounds having six or more carbon atoms are found in the product mixture obtained.

On the other hand, the proportion of compounds following reduction which have two hydroxyl groups is increased to 16% by weight, the proportion of compounds having three hydroxyl groups is increased to 20% and the proportion of compounds having four hydroxyl groups to 30%.

Various distributions of products can thus be obtained according to the invention by continuing the condensation of formaldehyde to residual formaldehyde contents varying from 8% to 1.5%. Any desired distribution of products necessary for a given field of application can thus be obtained.

The condensation reaction according to the invention is most advantageously carried out in a continuous cascade of stirrer vessels. In this variation of the process, the residual formaldehyde content can be exactly adjusted by varying the residence time in the individual vessels. The distribution of products in the reaction mixture and the average hydroxyl functionality of the mixture of polyhydric alcohols obtained from it by reduction can thus easily be varied within wide limits and with reproducible results.

The preparation according to the invention of a mixture of compounds containing hydroxyl groups can be carried out equally advantageously in a continuously operating reaction tube. To maintain the whole reaction volume at the desired pH, inorganic or organic base is continuously added in the necessary quantities at several points in the tube. In this case, the distribution of products and hydroxyl functionality of the resulting polyhydric alcohols can be varied within wide limits by varying the rate of flow through the tube. With this variation of the process it is, of course, also possible to obtain mixtures which contain predominantly higher molecular weight compounds and are free from colored by-products.

Mixtures containing predominant proportions of higher molecular weight products are also obtained when hydroxyaldehyde and hydroxyketone mixtures which contain predominantly low molecular weight components are subsequently post-treated with excess formaldehyde in the presence of an inorganic or organic base at a pH of from 9 to 13, preferably 10 to 11, for approximately 10 minutes to 12 hours at 10° to 100° C., preferably 30° to 60° C. By this method, not only are the low molecular weight compounds converted into higher molecular weight compounds by an alkaline catalyzed aldol reaction but, in addition, a higher proportion of branched hydroxy aldehydes and hydroxy ketones is obtained by additional methylolation on the carbon atom adjacent to the carbonyl group. These branched hydroxyketones and hydroxyaldehydes have a considerably larger number of primary hydroxyl groups than the corresponding straight chain compounds. The reactivity of these mixtures with compounds which react with hydroxyl groups is thereby considerably increased. This is advantageous for some purposes: For example, when compounds prepared according to the invention are reacted with organic isocyanates, the presence of primary hydroxyl groups causes a much more rapid formation of urethane than can be obtained with normal, straight chain polyhydric alcohols containing secondary hydroxyl groups.

If desired, the hydroxyaldehydes and hydroxyketones obtained by the process according to the invention can easily be converted into polyhydric alcohols by reduction in known manner; for example, the aqueous solution obtained may be directly reduced with sodium borohydride at room temperature or it may be reduced electrolytically.

Catalytic hydrogenation with hydrogen is another possible method. This may be carried out by any known methods for the reduction of sugars to sugar alcohols. Hydrogenation with Raney nickel in quantities of 5 to 20% by weight, based on the quantity of hydroxyaldehyde and hydroxyketone mixture to be reduced, at hydrogen pressures of 50 to 200 kg/cm² and temperatures of 20° to 200° C. is particularly suitable. However, catalysts containing nickel, cobalt, copper, platinum, rhodium or palladium on inert carriers may be used with equal success.

As already described above, the process according to the invention can be controlled by suitable adjustment of the pH so that a high proportion of the hydroxyaldehydes and hydroxyketones formed are reduced in situ to polyhydric alcohols by the formaldehyde present in the reaction mixture. Alternatively, the hydroxyaldehydes and ketones, which are formed in higher proportions by a slight deviation from the preferred pH control, may be subsequently reduced with formaldehyde. In that case, excess formaldehyde and an inorganic base are added to the reaction solution and the solution is stirred at from 10° to 100° C., preferably from 30° to 60° C., for a period of from 30 minutes to 12 hours while the pH is maintained 9 to 13, preferably 10 to 11. In this way, it is possible not only to reduce the carbonyl function but also, as already explained above, to synthesize higher molecular weight and branched chain products. Sodium hydroxide, potassium hydroxide, calcium and barium hydroxide and so-called crown either complexes of alkali metal atoms are preferred inorganic bases for accelerating the cross Cannizzaro reaction.

The reduction reaction may be further accelerated by cocatalysts. The compounds used for this purpose are preferably the oxalates of transition metals, in particular nickel, cobalt, iron, cadmium, zinc, chromium and manganese oxalate, and transition metals in the elementary form, e.g. nickel, cobalt, iron, copper, cadmium, zinc, chromium and manganese. It is particularly preferred to use activated nickel in the form of so-called Raney nickel and elementary zinc in the form of zinc powder.

Other suitable cocatalysts for the reduction with formaldehyde include amides of organic acids such as formamide, dimethylformamide and acetamide, and tetraalkyl ammonium salts, particularly tetramethylammonium chloride and tetraethylammonium chloride.

It may be economically particularly advantageous to carry out the process according to the invention immediately after formaldehyde production and utilize the heat stored in the formaldehyde vapor. A commonly employed commercial process for the production of formaldehyde, for example, proceeds according to the following reaction equation:

in which the reaction products are so strongly heated by the exothermic reaction that they are obtained in the gaseous form.

Summarizing, it is found that the process according to the invention affords the following important advantages over processes known in the art:

1. The process according to the invention gives rise to mixtures of hydroxyaldehydes, hydroxyketones and polyhydric alcohols in which the proportion of polyhydric alcohols, obtained by a crossed Cannizzaro reaction, is from 30 to 75% by weight. No unwanted decomposition products are formed. Hydrogenation or reduction of these mixtures is particularly economical and simple since only relatively small quantities of carbonyl groups need be converted into hydroxyl functional groups.

2. The process according to the invention gives rise to mixtures of polyols, hydroxyaldehydes and hydroxyketones with differing hydroxyl functionalities. The proportions of these compounds within the mixture can be varied as desired according to the envisaged use of the product. In particular, the process may be used for preparing mixtures which contain over 80% by weight, based on the quantity of formaldehyde put into the process, of compounds which have more than four carbon atoms. The high reproducibility of the distribution of products is also an important advantage over processes known in the art.

3. The process according to the invention gives rise to light colored or colorless products which can be hydrogenated without further purification or use for the other purposes described below. Purification of the product mixtures by distillation is not necessary.

4. The process according to the invention is particularly economical compared with processes known in the art. The use of highly concentrated formaldehyde solutions represent an additional saving in energy cost which would otherwise be required for evaporation of the solvent. Since virtually no unwanted side reactions occur in the process according to the invention, the products are obtained in yields of 95 to 98%, based on the quantity of formaldehyde put into the process.

Compared with the processes already known in the art, the process according to the invention proceeds at a very high velocity and therefore makes it possible for extremely high volume/time yields to be obtained.

5. The lead catalyst used in the process according to the invention can be used again, either immediately or after a simple working up process, so that there is no ecologically harmful accumulation of lead waste.

6. The products obtained by the process according to the invention have a lower viscosity and better properties for processing, depending on the nature and quantity of the polyhydric alcohols or polyhydroxyl compounds added.

7. The process according to the invention is distinguished by a particularly simple method of procedure since no catalyst is required.

8. The mixture of products obtainable by the process according to the invention are compatible with a very large number of compounds required for the manufacture of plastics, particularly with the fluorinated hydrocarbons used as blowing agents for foaming reactions.

The mixtures of hydroxyaldehydes and hydroxyketones obtainable according to the invention and the polyhydric alcohols produced from them by a cross Cannizzaro reaction or by hydrogenation are valuable starting materials for numerous products which have interesting commercial applications.

For example, the polyhydroxyl compounds obtained by reduction are very suitable for use as polyol components or cross-linking agents for the production of polyurethane resins from polyisocyanates, low molecular weight polyhydroxyl compounds and optionally higher molecular weight polyhydroxyl compounds, other chain lengthening agents, blowing agents, catalysts and other known additives.

The polyisocyanates used in this connection may be aliphatic, cycloaliphatic, araliphatic, aromatic or heterocyclic polyisocyanates such as those described, for example, by W. Siefken in Justus Liebigs Annalen der Chemie, 562, pages 75 to 136. These include, for example, ethylene diisocyanate, tetramethylene-1,4-diisocyanate, hexamethylene-1,6-diisocyanate, dodecane-1,12-diisocyanate; cyclobutane-1,3-diisocyanate, cyclohexane-1,3- and 1,4-diisocyanate and any mixtures of these isomers, 1-isocyanato-3,3,5-trimethyl-5-isocyanatomethyl-cyclohexane as described in German Auslegeschrift No. 1,202,785 and U.S. Pat. No. 3,401,190, hexahydrotolylene-2,4-diisocyanate and -2,6-diisocyanate and any mixtures of these isomers, hexahydrophenylene-1,3-diisocyanate and/or 1,4-diisocyanate; perhydrodiphenylmethane-2,4'-diisocyanate and/or 4,4'-diisocyanate; phenylene-1,3-diisocyanate; phenylene-1,3-diisocyanate and -1,4-diisocyanate; tolylene-2,4-diisocyanate and -2,6-diisocyanate and any mixtures of these isomers, diphenylmethane-2,4'-diisocyanate and/or 4,4'-diisocyanate; naphthylene-1,5-diisocyanate; triphenylmethane-4,4',4''-triisocyanate; polyphenylpolymethylene polyisocyanates which can be obtained by aniline formaldehyde condensation followed by phosgenation and which have been described, for example, in British Pat. Nos. 874,430 and No. 848,671, m- and p-isocyanatophenyl-sulphonyl isocyanates according to U.S. Pat. No. 3,454,606, perchlorinated aryl polyisocyanates such as those described, for example, in German Auslegeschrift 1,157,601 and U.S. Pat. No. 3,277,138, polyisocyanates having carbodiimide groups as described in German Pat. No. 1,092,007 and U.S. Pat. No. 3,152,162; diisocyanates of the kind described in U.S. Pat. No. 3,492,330; polyisocyanates with allophanate groups as described e.g. in British Pat. No. 994,890, Belgian Pat. No. 761,626 and published Dutch Patent Application 7,102,524; polyisocyanates with isocyanurate groups, e.g. as described in U.S. Pat. No. 3,001,973, German Pat. Nos. 1,022,789; 1,222,067 and 1,027,394 and German Offenlegungsschriften 1,929,034 and 2,004,048; polyisocyanates with urethane groups as described e.g. in Belgian Pat. No. 752,261 and U.S. Pat. No. 3,394,164, polyisocyanates with acylated area groups according to German Pat. No. 1,230,778, polyisocyanates with biuret groups as described e.g. in German Pat. No. 1,101,394; and U.S. Pat. Nos. 3,124,606 and 3,201,372 and British Pat. No. 889,050; polyisocyanates prepared by telomerization reactions as described, for example, in U.S. Pat. No. 3,654,106; polyisocyanates having ester groups such as those mentioned for example, in British Pat. Nos. 965,474 and 1,072,956; U.S. Pat. No. 3,567,763 and in German Pat. No. 1,231,688; reaction products of the above mentioned isocyanates with acetals according to German Pat. No. 1,072,385 and polyisocyanates containing polymeric fatty acid groups according to U.S. Pat. No. 3,455,883.

The distillation residues obtained from the commercial production of isocyanates and still containing isocyanate groups may also be used, optionally as solutions in one or more of the above mentioned polyisocyanates. Any mixtures of the above mentioned polyisocyanates may also be used.

As a general rule it is particularly preferred to use commercially readily available polyisocyanates such as tolylene-2,4-diisocyanate and -2,6-diisocyanate and any mixtures of these isomers ("TDI"), polyphenylpolymethylene polyisocyanates of the kind which can be prepared by aniline-formaldehyde condensation followed by phosgenation ("crude MDI") and polyisocyanates containing carbodiimide groups, urethane groups, allophanate groups, isocyanurate groups, urea groups or biuret groups ("modified polyisocyanates").

Any of the above mentioned polyols which have a molecular weight of from 400 to 10,000, preferably from 1000 to 6000, may be added as higher molecular weight polyhydroxyl compounds for the production of polyurethane resins from the products obtained according to the invention.

The starting components used according to the invention may also include compounds with a molecular weight of from 32 to 400 which have at least two hydrogen atoms capable of reacting with isocyanates. These also are compounds containing hydroxyl groups and/or amino groups and/or thiol groups and/or carboxyl groups, preferably hydroxyl groups and/or amino groups, and they serve as chain lengthening agents or cross-linking agents. They generally have from 2 to 8 hydrogen atoms capable of reacting with isocyanates, preferably 2 to 3 such hydrogen atoms.

The following are examples of such compounds: Ethylene glycol, propylene glycol-(1,2) and -(1,3), butylene glycol-(1,4) and -(2,3), pentanediol-(1,5), hexanediol- (1,6), octanediol-(1,8), neopentylglycol, 1,4-bis-hydroxymethylcyclohexane, 2-methyl-1,3-propanediol, glycerol, trimethylolpropane, hexanetriol-(1,2,6), trimethylolethane, pentaerythritol, quinitol, mannitol and sorbitol, diethylene glycol, triethylene glycol, tetraethylene glycol, polyethylene glycols with molecular weights of up to 400, dipropylene glycol, polypropylene glycols with molecular weights up to 400, dibutylene glycol, polybutylene glycols with molecular weights up to 400, 4,4'-dihydroxy-diphenylpropane, dihydroxymethylhydroquinone ethanolamine, diethanolamine, triethanolamine, 3-aminopropanol, ethylenediamine, 1,3-diaminopropane, 1-mercapto-3-aminopropane, 4-hydroxyphthalic acid, 4-aminophthalic acid, succinic acid, adipic acid, hydrazine, N,N-dimethylhydrazine, 4,4'-diaminodiphenylmethane, tolylenediamine, methylene-bis-chloroaniline, methylene-bis-anthranilic acid esters, diaminobenzoic acid ester and the isomeric chlorophenylenediamines.

In this case, again, there may be used mixtures of various compounds having molecular weights of from 32 to 400 and containing at least two hydrogen atoms capable of reacting with isocyanates.

When the polyhydroxyl compounds obtainable according to the invention are reacted on their own (without the addition of other isocyanate reactive components) with powerfully elasticizing polyisocyanates such as polyisocyanates which have a biuret structure (German Auslegeschrift No. 1,543,178), hard, light-fast, scratch-resistant and solvent-resistant surface coatings and lacquers are obtained.

Polyether alcohols with a high functionality can be obtained by propoxylation and/or ethoxylation of the polyols obtained according to the invention. Among these polyether alcohols, those with high hydroxyl numbers are suitable for the production of rigid or semirigid cellular polyurethane resins. Those with low hydroxyl numbers may be used as starting materials for highly elastic polyurethane foams.

Highly cross-linked polyesters which can be added to alkyd resins to improve their hardness can be obtained by reacting the mixtures of polyhydric alcohols prepared according to the invention with polybasic carboxylic acids of the kind mentioned above, e.g phthalic acid, isophthalic acid, terephthalic acid, tetra- and hexahydrophthalic acid, adipic acid or maleic acid by the usual methods of polyester condensation, for example as described in Houben-Weyl, Methoden der organischen Chemie, Vol. XIV, 12 page 40. The hydroxyl polyesters synthesized from hydroxyl compounds prepared according to the invention may, of course, also be used as starting components for the production of polyurethane resins.

The polyhydric alcohols as well as the hydroxyaldehydes and hydroxyketones prepared according to the invention can also be reacted very easily with long chain aliphatic monocarboxylic acids. Such compounds include caprylic, capric, lauric, myristic, palmitic, stearic, oleic, linoleic, arachidonic or behenic acid or their derivatives such as their metal or ethyl esters or their anhydrides or mixed anhydrides to form esters which contain hydroxyl groups. These hydroxyl esters resemble ethoxylation products of the polyols as well as the carbamic acid esters obtained as reaction products of the polyhydroxyl compounds according to the invention with long chain monoisocyanates such as n-octyl, n-decyl, n-dodecyl, myristyl, cetyl or stearyl isocyanate (see e.g. K. Linder, Tenside Vol. III, Wissenschaftliche Verlagsgesellschaft Stuttgart, 1964, page 2336) in being non-ionogenic surface active compounds which are valuable emulsifiers, wetting agents and plasticizers. The compounds according to the invention may also be used as moisturizers in cosmetics and plastics. They may also serve as antifreezes, for example.

The compounds may also be used as a carbohydrate containing substrate in nutrient media for microorganisms. Those products of the process which consist mainly of hydroxyaldehydes and hydroxyketones havng 5 and 6 carbon atoms are particularly suitable for this purpose.

Any of the usual catalysts, blowing agents and other additives (e.g. flame retarding agents, foam stabilizers, fillers, etc.) may, of course, also be used in the manufacture of polyurethane resins from the polyol mixtures obtained according to the invention. Additives of this kind has already been described, for example, in Kunststoff-Handbuch, Volume VII, published by Vieweg and Höchtlen, Carl-Hanser-Verlag, Munich 1966, e.g. on pages 96 to 113, 453 to 455 and 507 to 510.

It has also been surprisingly found that substantially impure formaldehyde-containing synthesis gases of the type formed in the commercial production of formaldehyde may be directly used in the process according to the invention as the formaldehyde source instead of aqueous formalin solutions.

The present invention therefore also relates to a process for the production of mixtures of low molecular weight polyhydroxyl compounds and, optionally, hydroxy aldehydes and hydroxy ketones by the condensation of formaldehyde in the presence of, as catalyst, from 0.01 to 10% by weight, based on formaldehyde, of a soluble or insoluble compound of a metal of the First to Eighth Secondary Group or of the Second to Fourth Main Group of the Periodic System of Elements, which may be fixed to a high molecular weight support and more than 10% by weight, based on formaldehyde, of one or more monohydric or polyhydric low molecular weight alcohols and/or relatively high molecular weight polyhydroxyl compounds. The pH-value of the reaction solution is kept between 5.5 and 9.0 by the controlled addition of one or more inorganic and/or organic bases up to a conversion of from 5 to 40%. It is subsequently adjusted to between pH 4.0 and pH 8.5 until the condensation reaction is terminated so that it is then 0.5 to 3.0 units lower than in the first phase of the reaction. The reaction is subsequently terminated at a residual formaldehyde content of from 0 to 10% by weight and the aldehyde and keto groups present in the reaction product optionally being reduced into hydroxyl groups. Formaldehyde-containing synthesis gases are used as the formaldehyde source.

Any synthesis gases of the type obtained in the commercial production of formaldehyde may be used for this embodiment of the process according to the invention. Examples of commercial processes for the manufacture of formaldehyde include the dehydrogenation of methanol and the oxidation of methanol on suitable catalysts, for example silver or iron molybdenum oxide, in the presence of air, optionally steam and formaldehyde exhaust gases. Another method is the oxidation of methane or ethylene or higher olefins or dimethyl ethers with air or oxygen-containing gases on suitable catalysts. These industrial synthesis gases generally contain as their main constituents from 20 to 70% by volume of nitrogen, 1 to 20% by volume of formaldehyde, 1 to 10% by volume of carbon dioxide and, in general, depending upon the manufacturing process, also relatively large quantities of steam. The remaining compounds are air, carbon monoxide, hydrogen and residues of starting products or of by-products such as methanol, methane, ethylene, higher olefins, methyl formate, dimethyl ether and acetals and semiacetals of formaldehyde. In many cases, formose mixtures show a tendency towards browning reactions in the presence of oxygen, so that oxygen-free synthesis gases are preferably used in accordance with the invention.

However, the synthesis gases formed during the commercial production of formaldehyde can be used in crude form, i.e. without any preliminary purification. This is particularly advantageous for economic reasons. Surprisingly, the large quantities of carbon dioxide present in the synthesis gases do not interfere with formose formation. Since most of the above-mentioned metals (e.g. the catalysts preferably used in the invention like calcium and lead) form insoluble carbonates in medium pH-ranges, it had been expected that these catalysts would be rapidly deactivated where formaldehyde-containing synthesis gases are used as the formaldehyde source. However, it has surprisingly been found that, in spite of the very large quantities of carbon dioxide present (frequently an approximately 300 to 600-fold molar excess of carbon dioxide relative to the metal catalyst) there is no interference with the catalytic activity of the metal ions. This can presumably be attributed to the surprisingly high ability of formose to form extremely stable complexes with a variety of different metal ions.

The process according to the invention wherein formaldehyde containing synthesis gases are used may be carried out both in batches and, preferably, continuously. The absorbents used for the formaldehyde in the synthesis gases are monohydric or polyhydric alcohols with a molecular weight of from 32 to 400 and/or polyhydroxyl compounds with a molecular weight of from 400 to 10,000. These absorption liquids may also contain water and up to 10% by weight, based on the formaldehyde to be absorbed, of co-catalysts based on compounds capable of enediol formation. The catalyst itself may be added in dissolved or suspended form to the absorption liquid. The process using the synthesis gases is generally carried out under normal pressure. If, for reasons associated with the intended applications of the products, strong caramelization and other secondary reactions such as rearrangements and sugar condensations, are desirable, it is also possible to work at elevated pressure and at temperatures of from 110° to 150° C. Pressures of from 5 to 150 bars, more especially from 10 to 70 bars, are preferred in this connection. However, the process according to this embodiment of the invention may also be carried out under reduced pressure with quenched synthesis gases. The temperature of the absorption liquid is generally in the range from 70° to 110° C., preferably in the range from 80° to 100° C. In special cases, however, it may be preferred to allow formose formation to take place at lower temperatures, for example between 10° and 55° C., preferably between 10° and 50° C. The synthesis gases are generally introduced into the absorption liquid at a temperature of from 90° to 250° C., preferably at a temperature of from 100° to 140° C. The heat reservoir of the synthesis gases, which accumulate during their production at a temperature of approximately 300° C. may be utilized in an energy-saving manner for partially dehydrating the products of the process. The effect of the large volumes of inert gas present in the synthesis gas as entraining agents for water is of particular advantage in this connection.

In cases where the process according to the invention is carried out in batches, the synthesis gas is passed through a column filled with the stationary absorption liquid. In order to accelerate the exchange of material between the two phases, the absorption column preferably contains a large-surface tower packing known per se, for example in the form of Raschig rings, saddle rings, sieve plates or fine-mesh wire gauzes. The fixed catalysts based on ion exchangers which are preferably used in the invention may of course also serve simultaneously as the tower packing in the absorption column. The synthesis gas is passed through the absorption column until the absorption liquid has been saturated, i.e. until relatively large quantities of formaldehyde together with the inert gases flow off from the head of the column. Since the water present in the synthesis gases is also taken up at the same time as the formaldehyde by the absorption liquid, a mixture of the alcohol used as absorption liquid, an aqueous formaldehyde solution, and semiacetals of formaldehyde with the alcohol which are in dissociation equilibrium with the free alcohol and the aqueous formaldehyde solution is obtained at the end of the absorption process. In cases where the absorption liquid already contains the catalyst necessary for the process according to the invention, formose formation actually begins during absorption of the formaldehyde. The advantage of this procedure is that a greater quantity of formaldehyde can be taken up by a given volume of absorption liquid. However, it is of course possible according to the invention to inroduce the synthesis gas into a catalyst-free absorption liquid up to saturation point and only then to start the reaction by adding the catalyst.

However, it is particularly economical to carry out the process according to the invention wherein synthesis gases are used continuously. To this end, the alcohol or polyhydroxyl compound used as absorption liquid is kept circulating and the absorption liquid is best passed in countercurrent to the hot synthesis gases. In this preferred procedure, too, it is advantageous to use packed columns, bubble-tray columns, sieve-plate columns or trickle-film columns known per se as the absorption columns. Bubble columns may of course also be used for the process according to the invention.

Both in the continuous and in the batch variant of the process, the average residence time of the formaldehyde-containing synthesis gas in the absorption columns is generally between 0.3 and 10 seconds and preferably between 0.6 and 3 seconds.

Figure 1:
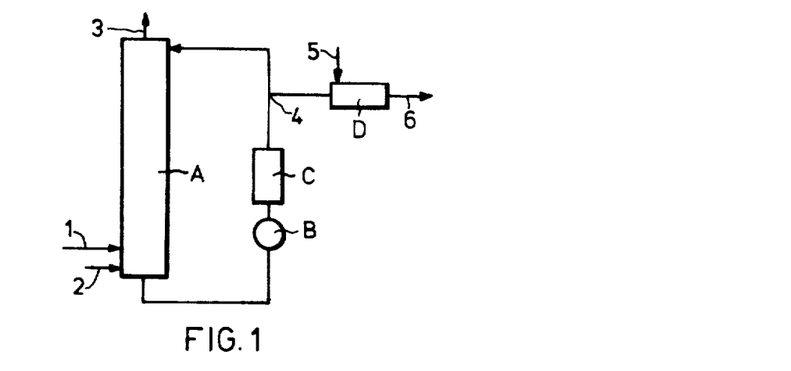
FIG. 1 schematically sets forth an apparatus suitable for carrying out the continuous process of the instant invention.

FIG. 1 shows in highly simplified, diagrammatic form an apparatus suitable for carrying out the continuous variation of the process according to the invention. The hot formaldehyde-containing synthesis gas is introduced at 1 into the absorption column A filled with absorption liquid. Additives such as, for example, catalyst, monohydric or polyhydric alcohols, relatively high molecular weight polyhydroxyl compound, inorganic or organic base, etc., may be introduced at 2. The absorption liquid is circulated by the pump B and passed in countercurrent to the synthesis gas. The steam-containing gases freed from formaldehyde leave the absorption column at 3. C represents a heatable and coolable residence vessel in which formose formation may take place, in the presence of catalyst. Part of the formaldehyde-containing absorption liquid is continuously run off at 4 and passed through another residence vessel D into which additives such as, for example, catalyst, co-catalyst, bases, acids, etc., may again be added at 5. Most of the formaldehyde condensation reaction generally takes place in the residence vessel D. The reaction product leaves the apparatus at 6.

In the continuous variation of the process according to this embodiment of the invention, both the metal catalyst and, optionally, a compound capable of enediol formation as co-catalyst may again be added to the absorption liquid, as mentioned above. In this case, the condensation of the formaldehyde into formose actually beings at the same time as absorption of the formaldehyde. It is also possible, however, to add the catalyst and, optionally, the co-catalyst after the product has been removed, i.e. for example at 5 in FIG. 1, so that formose formation takes place almost completely outside the circuit of the absorption liquid.

In the continuous variation of the process according to the invention using gaseous formaldehyde, it is necessary to differentiate between the starting phase and the stationary phase. During the starting phase of the process, the synthesis gas is passed through the recirculated absorption liquid which is a monohydric or, preferably, polyhydric alcohol or relatively high molecular weight polyhydroxyl compound. During this starting phase, the concentration of formaldehyde and water and optionally, where catalysts are present in the absorption liquid, of formose increases until finally a flow equilibrium is reached between the quantity of formaldehyde introduced by the synthesis gas and the quantity of formaldehyde (or formose) removed from the circuit. The duration of this starting phase is determined not only by the volume of the absorption column, pump, pipes and, optionally, the residence vessel, but also and, above all, by the composition of the absorption liquid during start-up. The starting phase may be considerably shortened by adding at the outset as much formalin solution and, optionally, formose to the absorption liquid as corresponds to the stationary phase. Depending upon the starting composition of the absorption liquid and the dimensions of the reactor, the starting phase lasts from a few seconds to about 2 hours and generally from 1 to 60 minutes.

The stationary formaldehyde concentration in the absorption liquid is, of course, determined on the one hand by the procedure adopted (formose formation actually taking place at the same time as absorption of the formaldehyde or alternatively outside the absorption apparatus) and on the other hand by the process parameters which are the volume of synthesis gas used per unit of time; the overall volume of the absorption liquid; the average residence time of the absorption liquid in the absorption column; temperature; pressure; hydroxyl functionality of the alcohol and concentration of the catalyst or co-catalyst used, if any. In general, however, the stationary formaldehyde concentration in the absorption column, where catalysts and optionally co-catalysts are present in the absorption liquid, amounts to between 0.5 and 10% by weight, especially between 1 and 5% by weight. If the catalyst is added to the absorption liquid outside the circuit, the stationary formaldehyde concentration in the circuit is, of course, also increased and generally amounts to between 2 and 70% by weight, preferably to between 10 and 50% by weight.

At the preferred process temperatures of about 80° to 100° C., approximately one third of the water emanating from the synthesis gas is evaporated by the heat of reaction liberated or entrained by the inert gases in the stationary phase. The residual water in the synthesis gases provides for a constant water content in the absorption liquid and during condensation of the formaldehyde. After the stationary phase has been reached, therefore, it is only necessary to add to the circuit, apart from the synthesis gas, such a quantity of monohydric or polyhydric low molecular weight alcohol or relatively high molecular weight polyhydroxyl compound and, optionally, catalyst, co-catalyst and inorganic or organic base to maintain the required pH-range, as is continuously removed from the circuit.

If formose formation takes place completely or partly outside the circuit of the absorption liquid, the condensation reaction of the formaldehyde may be allowed to take place in a continuous cascade of stirrer-equipped vessels. By varying the residence time in the individual stirrer-equipped vessels of the cascade, it is possible exactly to adjust the residual formaldehyde content in this variations of the process. The product distribution of the reaction mixture and the average hydroxyl functionality of the mixture of polyhydric alcohols obtainable therefrom by reduction may readily be varied within wide limits and reproduced in this way. It is also possible for condensation of the formaldehyde into formose to be carried out in tubular coil reactors rather than in cascades of stirrer-equipped vessels, under pressure of approximately 5 to 150 bars, preferably 10 to 70 bars ad at elevated temperatures of preferably 105° to 140° C. The dimensions of the tubular coil reactor must, of course, take into account the cubic expansion co-efficient of the formose mixtures formed in order to avoid producing extremely high liquid pressures. Suitable tubular coil reactors are described, for example, in German Auslegeschriften Nos. 1,667,051 and 1,921,045. An example of the use of these raw formaldehyde gases can be found in Example 16.

The following Examples serve to explain the process according to the invention. The numerical values are to be understood as parts by weight and percentages by weight unless otherwise specified.

EXAMPLES

EXAMPLE 1

500 parts of a 37% aqueous formalin solution (6.17 mol of formaldehyde) and 5 parts (0.013 mol) and lead-(II) acetate are heated to the reflux temperature. In another vessel, 124 parts (2.0 mol) of ethylene glycol are mixed with 1 part (0.006 mol) of potassium permanganate; heat is evolved as the two components are mixed. This mixture is poured into the boiling formalin solution, which is thereby acidified to pH 3.9. The heating bath is removed and a mixture of equal parts of potassium hydroxide and water (approximately 44% solution) is added dropwise to the reaction mixture until it has a pH of 8.5. At that point, the mixture begins to boil spontaneously.

The amount of potassium hydroxide solution used up ay this stage is 6.1 parts, calculated as solid potassium hydroxide.

Potassium hydroxide solution continues to be added dropwise to maintain the exothermic reaction. The alkali is added at such a rate that the pH of the reaction mixture is adjusted to and maintained at 6.9. After 20 minutes, the residual formaldehyde content of the solution has fallen to 5.8%. Total consumption of potassium hydroxide: 12.2 parts.

1.5 parts of sulphuric acid in 10 parts of water are added to inactivate the catalyst. Lead sulphate is thereby precipitated and the pH drops to 4.6. The reaction mixture is left to cool and then suction filtered to remove insoluble constituents. After concentration by evaporation in a water jet vacuum, 302 parts of a mixture of a polyhydric alcohols, hydroxy aldehydes and hydroxy ketones containing 10% of water having a viscosity at 50° C. of 51 mPa s and containing 33.9% of reducing constituents, calculated as glucose, are obtained.

A mixture of polyhydric alcohols is obtained from this aqueous mixture of alcohols, hydroxy aldehydes and hydroxy ketones by catalytic hydrogenation. According to gas chromatographic analysis, the alcohol mixture has the following distribution of components:

dihydric alcohols: 46.4% by weight
trihydric alcohols: 4.4% by weight
tetrahydric alcohols: 6.2% by weight
pentavalent alcohols: 14.8% by weight
hexavalent alcohols: 24.8% by weight
heptavalent and higher valent alcohols: 3.4% by weight

EXAMPLE 2

500 parts of a 37% aqueous formalin solution (6.17 mol of formaldehyde), 124 parts (2.0 mol) of ethylene glycol, 5 parts (0.013 mol) of lead(II) acetate and 5 parts of unreduced product mixture from Example 1 are heated to reflux. The heating bath is then removed. The subsequent procedure is identical to that of Example 1.

After a reaction time of 15 minutes, during which the pH was maintained at 7.2-7.5 (after a starting phase at pH 8.2), the reaction is stopped at a residual formaldehyde content of 0.6%. Potassium hydroxide consumption: 12.8 parts. 308 parts of a mixture of polyhydric alcohols, hydroxy aldehydes and hydroxyketones containing 10% of water and having a viscosity at 50° C. of 48 mPa s and containing 34.2% of reducing constituents, calculated as glucose, are obtained.

EXAMPLE 3

500 parts of a 37% aqueous formalin solution (6.17 mol of formaldehyde) are heated to reflux with 124 parts (2.0 mol) of ethylene glycol and 5 parts (0.013 mol) of lead(II) acetate. The heating bath is then removed. The subsequent procedure is identical to that of Example 1.

After a reaction time of 23 minutes, during which the pH was maintained at 6.9-7.1 (after a starting phase at pH 8.1), the reaction is stopped at a residual formaldehyde content of 0.3%. Potassium hydroxide consumption: 14.0 parts.

288 parts of a mixture of polyhydric alcohols, hydroxy aldehydes and hydroxy ketones containing 10% of water and having a viscosity at 50° C. of 46 mPa s and containing 38.4% of reducing constituents, based on glucose, are obtained.

EXAMPLE 4

1800 parts (18.5 mol of formaldehyde) of a 37% aqueous formalin solution and 1780 parts of a polyether (A) with an average molecular weight of 305 which has been started on saccharose and propylene glycol and has been propoxylated to OH No. 550 in the presence of sodium alcoholate are heated to boiling with 18 parts of the unreduced product mixture from Example 1 and 18 parts (0.047 mol) of lead(II) acetate. The heating bath is removed and 30 parts of an organic mixture of bases consisting of 75% of ethyl diethanolamine, 17% of ethyl-(2-hydroxyethyl-oxyethyl)-ethanolamine and 7% of ethyl-(2-hydroxyethyl-oxyethyl)-amine are slowly added dropwise, the pH being adjusted first to 6.4 and then to 4.6. The reaction is stopped after 90 minutes, at a residual formaldehyde content of 0.3%. The lad is removed by precipitation with sulphuric acid. The mixture is concentrated by evaporation in a water jet vacuum. 2700 g of a polyether (B) which has been started on ethylene diamine and has been propoxylated to OH No. 500 are added. 5177 parts of a polyol mixture having a water content of 4.9%, an OH No. 496 and a viscosity at 25° C. of 2.634 Pa s are obtained. After the addition of stabilizers and blowing agents, this mixture is ready for foaming, e.g. with crude diphenylmethane diisocyanate (MDI).

EXAMPLE 5

3000 parts of a 37% aqueous formalin solution (37 mol of formaldehyde), 2960 parts of polyether (A) described in Example 4, 150 parts of ε-caprolactam, 30 parts of the unreduced product mixture from Example 1 and 30 parts (0.081 mol) of lead(II) acetate are heated under reflux. An organic mixture of bases consisting of 75% of ethyl diethanolamine, 17% of ethyl-(2-hydroxyethyl oxyethyl)-ethanolamine and 7% of ethyl-bis-(2-hydroxyethyl oxyethyl)-amine are then slowly added dropwise. 56 parts of the mixture of bases are used up.

After a reaction time of 45 minutes, during which the pH was kept at 5.6-5.8 (after a starting phase at 7.1), the reaction is stopped at a residual formaldehyde content of 0.3%.

After cooling and removal of the precipitated lead sulphate by suction filtration, 4440 parts of the polyether (B) indicated in Example 4 are added.

8267 parts of a polyol mixture having a water content of 0.3% and a viscosity at 25° C. of 9.331 Pa.s are obtained. After the addition of stabilizers and blowing agents, this polyol mixture is ready for foaming, for example with crude MDI.

EXAMPLE 6

1418 parts of a 37% aqueous formalin solution (17.5 mol of formaldehyde), 2114 parts of polyether (A) indicated in Example 4, 423 parts of ε-caprolactam, 180 parts of the unreduced product mixture from Example 1 and 18 parts (0.049 mol) of lead(II) acetate are heated to reflux. The subsequent procedure is identical to that of Example 1. Potassium hydroxide consumption: 13.2 parts.

After a reaction time of 35 minutes, during which the pH was adjusted to 5.4-5.5 (after a starting phase at 7.3), the reaction is stopped at a residual formaldehyde content of 0.3%.

2529 parts of a mixture containing 3.2% of water and 14.0%, based on glucose, of reducing constituents and having a viscosity at 50° C. of 309 mPa.s are obtained. This mixture is compatible with fluorinated hydrocarbons.

EXAMPLE 7

1000 parts of a 37% aqueous formalin solution (12.3 mol of formaldehyde), 2629 parts of polyether (A) indicated in Example 4, 526 parts of ε-caprolactam, 100 parts of the unreduced product mixture from Example 1, 394 parts (6.4 mol) of ethylene glycol and 10 parts (0.026 mol) of lead(II) acetate are heated to reflux. The subsequent procedure is identical to that of Example 1. Potassium hydroxide consumption: 7.2 parts.

After a reaction time of 15 minutes, during which the pH was adjusted to 6.0 (after a starting phase at 7.2), the reaction is stopped at a residual formaldehyde content of 0.3%. 3802 parts of a mixture containing 3.2% of water and 6.5%, based on glucose, of reducing constituents and having a viscosity at 50° C. of 104.9 mPa.s are obtained. This mixture is compatible with fluorinated hydrocarbons.

EXAMPLE 8

1000 parts of a 37% aqueous formalin solution (12.3 mol of formaldehyde), 2629 parts of polyether (A) indicated in Example 4, 526 parts of ε-caprolactam, 100 parts of the unreduced product mixture from Example 1, 200 parts (3.22 mol) of ethylene glycol, 200 parts (2.17 mol) of glycerol and 10 parts (0.026 mol) of lead(II) acetate are heated to boiling. The procedure is otherwise identical to that of Example 1. Sodium hydroxide consumption: 28 parts.

After a reaction time of 15 minutes, during which the pH was adjusted to 6.1–6.3 (after a starting phase at 7.1), the reaction is stopped at a residual formaldehyde content of 0.2%.

3492 parts of a mixture containing 3.2% of water and 6.9%, based on glucose, of reducing constituents and having a viscosity at 50° C. of 208 mPa.s are obtained. This mixture is compatible with fluorinated hydrocarbons.

EXAMPLE 9

1000 parts of a 37% aqueous formalin solution (12.3 mol of formaldehyde), 2629 parts of polyether (A) indicated in Example 4, 562 parts of ε-caprolactam, 100 parts of the unreduced product mixture from Example 1, 400 parts (4.34 mol) of glycerol and 10 parts (0.026 mol) of lead(II) acetate are heated to boiling. The procedure is otherwise identical to that of Example 1. Potassium hydroxide consumption: 7.3 parts.

After a reaction time of 17 minutes, during which the pH was adjusted to 5.3–5.8 (after a starting phase at 6.8), the reaction is stopped at a residual formaldehyde content of 0.4%.

3869 parts of a mixture containing 3.2% of water and 6.9%, based on glucose, of reducing constituents and having a viscosity at 50° C. of 222 mPa.s are obtained. This mixture is highly compatible with fluorinated hydrocarbons.

EXAMPLE 10

609 parts of a 37% aqueous formalin solution (7.5 mol of formaldehyde), 1600 parts of a polyether (C) having an average molecular weight of 450 which has been started on saccharose, propylene glycol and water and propoxylated to OH No. 380 in the presence of sodium alcoholate, 320 parts of ε-caprolactam, 60 parts of the unreduced product mixture from Example 1, 240 parts (3.87 mol) of ethylene glycol and 6 parts (0.0156 mol) of lead(II) acetate are heated to boiling. The procedure is otherwise identical to that of Example 1. Sodium hydroxide consumption: 6.1 parts.

After a reaction time of 10 minutes, during which the pH was adjusted to 5.9 (after a starting phase at 7.2), the reaction is stopped at a residual formaldehyde content of 0.1%.

2367 parts of mixture containing 3.2% of water and 3.3%, based on glucose, of reducing constituents and having a viscosity at 50° C. of 110 mPa.s are obtained. This mixture is compatible with fluorinated hydrocarbons.

EXAMPLE 11

1000 parts of a 37% aqueous formalin solution (12.3 mol of formaldehyde), 2629 parts of polyether (C) described in Example 10, 526 parts of ε-caprolactam, 100 parts of the unreduced product mixture from Example 1, 200 parts (3.22 mol) of ethylene glycol, 200 parts (2.17 mol) of glycerol and 10 parts (0.026 mol) of lead(II) acetate are heated to boiling. The procedure is otherwise identical to that of Example 1. Sodium hydroxide consumption: 7.9 parts.

After a reaction time of 17 minutes, during which the pH is adjusted to 5.4–5.6 (after a starting phase at 6.9), the reaction is stopped at a residual formaldehyde content of 0.2%.

3880 parts of a mixture containing 3.2% of water and 5.6%, based on glucose, of reducing constituents and having a viscosity at 50° C. of 95 mPa.s are obtained. The mixture is compatible with fluorinated hydrocarbons.

EXAMPLE 12

1000 parts of a 37% aqueous formalin solution (12.3 mol of formaldehyde), 2629 parts of polyether (C) described in Example b 10, 526 parts of ε-caprolactam, 100 parts of the unreduced product mixture from Example 1, 400 parts (4.34 mol) of glycerol and 10 parts (0.026 mol) of lead(II) acetate are heated to boiling. The procedure is otherwise identical to that of Example 1. Sodium hydroxide consumption: 7.3 parts.

After a reaction time of 15 minutes, during which the pH was adjusted to 5.5–5.8 (after a starting phase of 7.1), the reaction is stopped at a residual formaldehyde content of 0.3%.

3876 parts of a mixture containing 3.2% of water and 6.6%, based on glucose, of reducing constituents and having a viscosity at 50° C. of 136 mPa.s are obtained. The mixture is compatible with fluorinated hydrocarbons.

EXAMPLE 13

1035 parts of 37% aqueous formalin solution (12.8 mol of formaldehyde), 498 parts of polyether (A) indicated in Example 4, 1035 parts of a polyether (D) with an average molecular weight of 6000 which has been started on trimethylol propane and propoxylated to OH No. 50 with propylene oxide in the presence of potassium hydroxide, and then ethoxylated to OH number 28, 115 parts of the unreduced product mixture from Example 1, 306 parts of ε-caprolactam and 11.5 parts (0.03 mol) of lead(II) acetate are heated to boiling. The procedure is otherwised identical to that of Example 1.

Potassium hydroxide consumption: 20.7 parts

After a reaction time of 30 minutes, during which the pH was adjusted to 4.8–5.2 (after a starting phase at 6.4), the reaction is stopped at a residual formaldehyde content of 0.03%.

2154 parts of an emulsion containing 0.8% of water and 13.4%, based on glucose, of reducing constituents and having an OH No. of 447 are obtained.

EXAMPKLE 14

945 parts of a 37% aqueous formalin solution (11.7 mol of formaldehyde) are heated to boiling with 1000 parts of polyether (A) indicated in Example 4, 667 parts of polyether (D) indicated in Example 14, 120 parts of the unreduced product mixture from Example 1, 282 parts of ε-caprolactam and 12 parts (0.032 mol) of lead-(II) acetate. The procedure is otherwise identical to that of Example 1. Potassium hydroxide consumption: 15.9 parts After a reaction time of 15 minutes, during which the pH was adjusted to 5.5–5.6 (after a starting phase of 6.7), the reaction is stopped at a residual formaldehyde content of 0.15%.

2055 parts of an emulsion containing 0.8% of water and 12.4%, based on glucose, of reducing constituents and having an OH No. of 521 are obtained.

EXAMPLE 15

Figure 2:
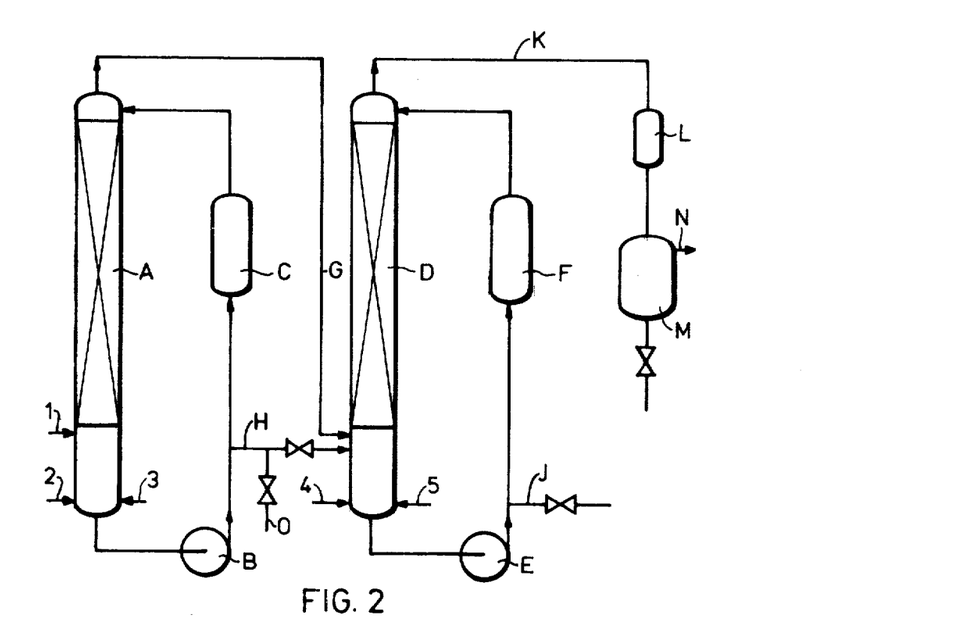

The apparatus used for this Example is diagrammatically illustrated in FIG. 2. The absorption columns have a diameter of 100 mm and a height of 2.35 m and are filled with clay saddles.

Approximately 25 kg of the particular absorption liquid are introduced initially into the sump of the absorption column A having a capacity of approximately 30 liters. The absorption liquid is circulated by means of a pump B with a throughout of approximately 700 l/h and heated to 78° C. by means of an external heat exchanger C which provides for both heating and cooling. Another 25 kg of the absorption liquid are initially introduced into the sump of the absorption column D. By means of a pump E with a throughput of approximately 300 l/h, the absorption liquid is also preheated to 78° C. through a heatable and coolable heat exchanger F. Once this temperature has been reached in both absorption columns, formaldehyde-containing process gas, at a temperature of approximately 85° C., is introduced into the absorption column A at 1 in a quantity of 21.33 $Nm^3/h$ and introduced from the absorption column A through the gase pipe G into the absorption column D.

The formaldehyde synthesis gas has the following composition:

|  | $Nm^3/h$ | Vol. % |
|---|---|---|
| $N_2$ | 6.73 | 31.607 |
| $H_2$ | 1.35 | 6.441 |
| $CO_2$ | 0.31 | 1.477 |
| CO | 0.02 | 0.099 |
| $O_2$ | 0.01 | 0.066 |
| HC—OCH₃ | | |
| $CH_4$ | 0.01 | 0.066 |
| $CH_2O$ | 3.83 | 17.565 |
| $H_2O$ | 8.93 | 42.012 |
| $CH_3OH$ | 0.14 | 0.667 |
| | 21.33 $Nm^3/h$ | 100.000 Vol. % |

In order to keep the level of the sump constant, the absorption liquid from absorption column A is continuously run off through pipe H into the absorption column D. From the sump of the absorption column B, the absorption liquid containing from 37 to 49% by weight of formaldehyde, depending upon the residence time, is continuously run off through pipe I. A corresponding quantity of fresh absorption liquid is introduced into the absorption columns A and B, at 2 and 4 respectively.

The exhaust gases leaving the head of the column B are delivered through the pipe K to the heat exchanger L and the separator M.

After the formaldehyde-containing synthesis gases have been passed for 2 hours through various catalyst-free absorption liquids, the following absorption yields are obtained:

| Absorption liquid | Formaldehyde absorbed (% by weight) |
|---|---|
| Ethylene glycol | 99 |
| Glycerol/water (1:1) | 99 |
| Diethylene glycol | 97.8 |
| Triethylene glycol | 97 |
| Propylene glycol | 97 |
| Formose I/ethylene glycol (1:1) | 99.3 |
| Formose II/glycerol/water (2:1:1) | 99 |

Formose I has the following distribution of components:

Compounds containing 2 carbon atoms: 0.2% by weight

Compounds containing 3 carbon atoms: 2.6% by weight

Compounds containing 4 carbon atoms: 4.6% by weight

Compounds containing 5 carbon atoms: 24.8% by weight

Compounds containing 6 carbon atoms: 44.5% by weight

Compounds containing 7 and more carbon atoms: 23.5% by weight

Formose II has the following molecular distribution:

Compounds containing 2 carbon atoms: 16.8% by weight

Compounds containing 3 carbon atoms: 21.0% by weight

Compounds containing 4 carbon atoms: 29.9% by weight

Compounds containing 5 carbon atoms: 25.1% by weight

Compounds containing 6 and more carbon atoms: 7.2% by weight

The formaldehyde-containing absorption liquids leaving the absorption apparatus at 1 are indefinitely stable in storage. They may be condensed into formose/alcohol mixtures, for example in accordance with Examples 1 to 14 above, by adding lead acetate as catalyst, sodium hydroxide and, optionally, co-catalyst.

What is claimed is:

1. In a process for the preparation of a mixture of low molecular weight polyhydroxyl compounds and optionally hydroxy aldehydes and hydroxy ketones by the condensation of formaldehyde hydrate, in the presence of from 0.01–10% by weight, based on formaldehyde, of metal compounds as catalyst, and from 0–10% by weight, based on formaldehyde, of co-catalysts which are based on compounds capable of enediol formation, the improvement which comprises condensing formaldehyde hydrate at a reaction temperature of from 10°–150° C. in the presence of I. a soluble or insoluble compound of a metal of the first to eighth sub-group or second to fourth main group of the Periodic System of Elements, optionally bound to a high molecular weight carrier, and II. more than 10% by weight, based on formaldehyde, of one or more dihydric or higher hydric low molecular weight alcohols and/or higher molecular weight polyhydroxyl compounds, maintaining the pH of the reaction solution between 5.5 and 9.0 by controlled addition of one or more inorganic and/or organic bases up to a conversion rate of 5–40% by weight, lowering the pH of from 0.5 to 3 units and thereafter maintaining the pH at from 4.0–8.5 until the termination of the condensation reaction;

then stopping the reaction in known manner by inactivation of the catalyst when the residual formaldehyde content is from 0–10% by weight;

removing the catalyst and, optionally, reducing the aldehyde and keto groups present in the reaction product to hydroxyl groups.

2. The process of claim 1 wherein aqueous formaldehyde solutions and/or paraformaldehyde dispersions containing from 20 to 65% by weight of formaldehyde are used as the source of formaldehyde.

3. The process of claim 2 wherein the pH in the second stage of the reaction is lower by 0.5 to 3.0 units than in the first reaction phase.

4. The process of claim 1 wherein formaldehyde-containing synthesis gases are used as the formaldehyde source.

5. The process of claim 1, wherein from 0.1–10% by weight, based on formaldehyde, of co-catalysts are included in the reaction mixture.

6. The process of claim 1, wherein from 0.5–5% by weight, based on formaldehyde, of co-catalysts are included in the reaction mixture.

7. The process of claim 1 wherein the co-catalysts used are mixtures of hydroxy aldehydes and hydroxy ketones of the kind which are formed by the condensation of formaldehyde and which contain at least 75% by weight of $C_3$–$C_6$ compounds and are characterized by the following molar ratios:

Compounds with 3 C-atoms/compounds with 4 C-atoms: 0.5:1–2.0:1

Compounds with 4 C-atoms/compounds with 5 C-atoms: 0.2:1–2.0:1

Compounds with 5 C-atoms/compounds with 6 C-atoms: 0.5:1–5.0:1.

8. The process of claim 1, wherein the catalysts used are ion-exchangers charged with metal ions.

9. The process of claim 1, wherein component II consists entirely or partly of alcohols which have at least 2 adjacent hydroxyl groups.

10. Process according to claim 1, characterized in that one or more dihydric or higher hydric alcohols are added as component II in such quantities that the reaction mixture contains betweend 0.1 and 500 OH equivalents per mol of formaldehyde.

11. The process of claim 1, wherein the hydroxy aldehydes and hydroxy ketones present in the reaction products are subsequently reduced with formaldehyde by a crossed Cannizzaro reaction at a pH range of 9–13.

12. The process of claim 1, wherein the formaldehyde condensation is carried out continuously in a cascade of stirrer vessels.

13. The process of claim 1, wherein the condensation of formaldehyde is carried out continuously in a reaction tube.

14. A process for the production of mixtures of low molecular weight polyhydroxyl compounds and, optionally, hydroxy aldehydes and hydroxy ketones comprising condensing formaldehyde-containing synthesis gases in the presence of (I) as catalyst, from 0.01 to 10% by weight based on formaldehyde, of a soluble or insoluble compound of a metal of the First to Eighth Secondary Group or of the Second to Fourth Main Group of the Periodic System of Elements, optionally fixed to high molecular weight supports, and (II) more than 10% by weight, based on formaldehyde, of one or more monohydric or polyhydric low molecular weight alcohols and/or relatively high molecular weight polyhydroxyl compounds, at a temperature of 10° to 150° C., the pH-value of the reaction solution being kept between 5.5 and 9.0 by the controlled addition of one or more inorganic and/or organic bases up to a conversion of from 5% to 40% and subsequently being adjusted to between pH 4.0 and pH 8.5 until the condensation reaction is terminated and subsequently terminating the reaction at a residual formaldehyde content of from 0 to 10% by weight.

15. In a process for the production of polyurethane resins comprising reacting (a) Polyisocyanates with (b) low molecular weight polyhydroxyl compounds and optionally higher molecular weight polyhydroxyl compounds and, optionally, (c) other chain-lengthening agents, optionally in the presence of (d) blowing agents, catalysts and other known additives, the improvement which comprises using as component (b), mixtures of polyols prepared according to claim 1.

* * * * *